(12) United States Patent
Murai et al.

(10) Patent No.: US 12,268,798 B2
(45) Date of Patent: Apr. 8, 2025

(54) METHOD FOR SCREENING OF UNPLEASANT ODOR MASKING AGENTS

(71) Applicant: Takasago International Corporation, Tokyo (JP)

(72) Inventors: Masato Murai, Kanagawa (JP); Ikuo Terada, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 899 days.

(21) Appl. No.: 17/443,737

(22) Filed: Jul. 27, 2021

(65) Prior Publication Data

US 2022/0034866 A1     Feb. 3, 2022

(30) Foreign Application Priority Data

Jul. 28, 2020  (JP) ................ 2020-127591
Oct. 16, 2020  (JP) ................ 2020-174788

(51) Int. Cl.
  *G01N 33/50*   (2006.01)
  *A61L 9/01*    (2006.01)
  *C12Q 1/66*    (2006.01)

(52) U.S. Cl.
  CPC .............. *A61L 9/01* (2013.01); *G01N 33/502* (2013.01); *A61L 2209/21* (2013.01); *C12Q 1/66* (2013.01); *G01N 2333/705* (2013.01)

(58) Field of Classification Search
  CPC ... G01N 33/502; G01N 2333/705; C12Q 1/66
  See application file for complete search history.

(56) References Cited

U.S. PATENT DOCUMENTS

| | | | |
|---|---|---|---|
| 7,923,585 B2 | 4/2011 | Ishida et al. | |
| 8,071,531 B2 | 12/2011 | Aida et al. | |
| 8,309,062 B2 | 11/2012 | Hojo et al. | |
| 8,377,458 B2 | 2/2013 | Komatsuki et al. | |
| 8,476,472 B2 | 7/2013 | Hojo et al. | |
| 8,632,792 B2 | 1/2014 | Ishida et al. | |
| 8,741,275 B2 | 6/2014 | Dente et al. | |
| 2003/0092599 A1 | 5/2003 | Suganuma et al. | |
| 2003/0130164 A1 | 7/2003 | Markert et al. | |
| 2003/0158080 A1 | 8/2003 | Matsuda et al. | |
| 2005/0244445 A1 | 11/2005 | Anderson | |
| 2012/0101020 A1 | 4/2012 | Wiedemann et al. | |
| 2013/0303432 A1 | 11/2013 | Holscher et al. | |
| 2017/0181935 A1 | 6/2017 | Cropper et al. | |
| 2017/0196786 A1 | 7/2017 | Naser et al. | |
| 2020/0056118 A1 | 2/2020 | Schulze et al. | |
| 2020/0318205 A1 | 10/2020 | Miki et al. | |
| 2021/0179970 A1 | 6/2021 | Kao et al. | |

FOREIGN PATENT DOCUMENTS

| | | |
|---|---|---|
| EP | 1 793 796 | 6/2007 |
| EP | 1 884 251 A1 | 2/2008 |
| JP | 2000-281509 A | 10/2000 |
| JP | 2003-190264 A | 7/2003 |
| JP | 2008-036434 A | 2/2008 |
| JP | 2008-136841 A | 6/2008 |
| JP | 2012-250958 A | 12/2012 |
| JP | 2017-176134 A | 10/2017 |
| RU | 2592351 C2 | 3/2016 |
| WO | WO-2006/032668 A1 | 3/2006 |
| WO | WO-2019/131789 A1 | 7/2019 |

OTHER PUBLICATIONS

Eric Block, J. Agricultural and Food chem. 2018, 66: 13346-13366).*
Floriano et al., Chem. Senses 29: 269-290, 2004.*
Alberto B. Prudencio, dianas, vol. 2, e20130302 pp. 1-6, (2013).*
Bendall, Justin G., "Aroma Compounds of Fresh Milk from New Zealand Cows Fed Different Diets," J. Agric. Food Chem., 2001, 49(10):4825-4832.
De March et al., "Structure-odour relationships reviewed in the postgenomic era," Flavour and Fragrance Journal, May 31, 2015, 30:342-361.
Horio et al., "Contribution of individual olfactory receptors to odor-induced attractive or aversive behavior in mice," Nature Communications, 2019, 10:209, 9 pages.
Keller et al., "Genetic variation in a human odorant receptor alters odour perception," Nature, Sep. 27, 2017, 449:468-472.
Shimoda et al., "Studies on Off-Flavor Formed during Storage of Satsuma Mandarin Juice (Part II)," Nippon Nogeikagaku Kaishi, 1981, 55(1):23-30.
U.S. Appl. No. 17/443,743, filed Jul. 27, 2021, Mihara et al.
Araneda et al., "The molecular receptive range of an odorant receptor," Nature Neuroscience, Dec. 2000, 3(12):1248-1255.
Cooke et al., "Time profile in putrescine, cadaverine, indole and skatole in human saliva," Archives of Oral Biology, 2003, 48(4):323-327.
Markt et al., "Sniffing out significant "Pee values": genome wide associate study of asparagus anosmia," BMJ, 2016, i6071:1-5.

(Continued)

*Primary Examiner* — Gyan Chandra

(74) *Attorney, Agent, or Firm* — Foley & Lardner LLP

(57) ABSTRACT

The present invention relates to a method for screening a candidate substance for an unpleasant odor masking agent from among test substances using an olfactory receptor that is responsive to an unpleasant odor-causing substance. The screening method of the present invention includes the steps of:
  adding a test substance and an unpleasant odor-causing substance to an olfactory receptor polypeptide selected from the group consisting of OR2L3 and polypeptides which comprise an amino acid sequence having at least 80% identity to an amino acid sequence of OR2L3 and are responsive to the unpleasant odor-causing substance;
  measuring a response of the olfactory receptor polypeptide to the unpleasant odor-causing substance; and
  identifying the test substance that suppresses the response of the olfactory receptor polypeptide as a candidate substance for the unpleasant odor masking agent based on the measured response.

4 Claims, 6 Drawing Sheets

Specification includes a Sequence Listing.

(56) References Cited

OTHER PUBLICATIONS

Reddy et al., "Antagonism in olfactory receptor neurons and its implications for the perception of odor mixtures," eLife, Apr. 24, 2018, 7:1-23.
Verbeurgt et al., "Profiling of Olfactory Receptor Gene Expression in Whole Human Olfactory Mucosa," PLoS ONE, 2014, 9(5): e96333, 14 pages.
Pubchem (https://pubchem.ncbi.nlm.nim.nih.gov/compound/6438195#section=Depositor-Supplied-Synonyms&fullscreen=true) accessed Aug. 22, 2023, p. 102 (Year: 2023).
Webbook (https://webbook.nist.gov/cgi/cbook.cgi?ID=C16409431&Mask=200) accessed Aug. 22, 2023, p. 1-2 (Year: 2023).

* cited by examiner

SEQUENCE LISTING

<160> NUMBER OF SEQ ID NOS: 4

<210> SEQ ID NO 1
<211> LENGTH: 939
<212> TYPE: DNA
<213> ORGANISM: Homo sapiens
<220> FEATURE:
<221> NAME/KEY: CDS
<222> LOCATION: (1)..(939)

<400> SEQUENCE: 1

```
atg gaa aat tac aat caa aca tca act gat ttc atc tta tta gga ttc      48
Met Glu Asn Tyr Asn Gln Thr Ser Thr Asp Phe Ile Leu Leu Gly Phe
1               5                   10                  15 ttc cca cca tca aga att ggc ctt ttc ctc ttc atc ctc att gtt ttc      96
Phe Pro Pro Ser Arg Ile Gly Leu Phe Leu Phe Ile Leu Ile Val Phe
            20                  25                  30 att ttc cta atg gct cta att gga aac cta tcc atg att ctt ctc atc     144
Ile Phe Leu Met Ala Leu Ile Gly Asn Leu Ser Met Ile Leu Leu Ile
        35                  40                  45 ttc ttg gac acc cat ctc cac aca ccc atg tat ttc cta ctt agt cag     192
Phe Leu Asp Thr His Leu His Thr Pro Met Tyr Phe Leu Leu Ser Gln
```

```
             50                  55                  60
ctc tcc ctc att gac cta aat tac atc tcc acc att gtt cct aag atg    240
Leu Ser Leu Ile Asp Leu Asn Tyr Ile Ser Thr Ile Val Pro Lys Met
 65                  70                  75                  80 gca tct gat ttt ctg tct ggt aac aag tct atc tcc ttc act ggg tgt    288
Ala Ser Asp Phe Leu Ser Gly Asn Lys Ser Ile Ser Phe Thr Gly Cys
                 85                  90                  95 ggg att cag agt ttc ttc ttc tcg gca tta gga ggt gca gaa gca cta    336
Gly Ile Gln Ser Phe Phe Phe Ser Ala Leu Gly Gly Ala Glu Ala Leu
            100                 105                 110 ctt ttg gca tct atg gcc tat gat cgt tac att gct att tgc ttt cct    384
Leu Leu Ala Ser Met Ala Tyr Asp Arg Tyr Ile Ala Ile Cys Phe Pro
        115                 120                 125 ctt cac tat ccc atc cgc atg agc aaa aga atg tgt gtg ctg atg ata    432
Leu His Tyr Pro Ile Arg Met Ser Lys Arg Met Cys Val Leu Met Ile
    130                 135                 140 aca ggg tct tgg atc ata ggc tcg atc aat gct tgt gct cac act gta    480
Thr Gly Ser Trp Ile Ile Gly Ser Ile Asn Ala Cys Ala His Thr Val
145                 150                 155                 160 tat gta ctc cat att cct tat tgc caa tcc agg gcc atc aat cat ttc    528
Tyr Val Leu His Ile Pro Tyr Cys Gln Ser Arg Ala Ile Asn His Phe
                165                 170                 175 ttc tgt gat gtc cca gca atg gtg act ctg gcc tgc atg gac acc tgg    576
Phe Cys Asp Val Pro Ala Met Val Thr Leu Ala Cys Met Asp Thr Trp
            180                 185                 190 gtc tat gag ggc aca gtg ttt ttg agc acc acc atc ttt ctc gtg ttt    624
Val Tyr Glu Gly Thr Val Phe Leu Ser Thr Thr Ile Phe Leu Val Phe
        195                 200                 205 ccc ttc att gct att tca tgt tcc tat ggc cgg gtt ctc ctt gct gtc    672
Pro Phe Ile Ala Ile Ser Cys Ser Tyr Gly Arg Val Leu Leu Ala Val
    210                 215                 220 tac cac atg aaa tct gca gaa ggg agg aag aaa gcc tac ctg acc tgc    720
Tyr His Met Lys Ser Ala Glu Gly Arg Lys Lys Ala Tyr Leu Thr Cys
225                 230                 235                 240 agc acc cac ctc act gta gta act ttc tac tat gca cct ttt gtc tac    768
Ser Thr His Leu Thr Val Val Thr Phe Tyr Tyr Ala Pro Phe Val Tyr
                245                 250                 255 act tat cta cgt cca aga tcc ctg cga tct cca aca gag gac aag gtt    816
Thr Tyr Leu Arg Pro Arg Ser Leu Arg Ser Pro Thr Glu Asp Lys Val
            260                 265                 270 ctg gct gtc ttc tac acc acc ctc act cca atg ctc aac ccc atc atc    864
Leu Ala Val Phe Tyr Thr Thr Leu Thr Pro Met Leu Asn Pro Ile Ile
        275                 280                 285 tat agc ctg agg aac aag gag gtg atg ggg gcc ctg aca cga gtg agt    912
Tyr Ser Leu Arg Asn Lys Glu Val Met Gly Ala Leu Thr Arg Val Ser
    290                 295                 300 cag aga atc tgc tct ggg aaa atg tag                                939
Gln Arg Ile Cys Ser Gly Lys Met
305                 310

<210> SEQ ID NO 2
<211> LENGTH: 312
<212> TYPE: PRT
<213> ORGANISM: Homo sapiens

<400> SEQUENCE: 2

Met Glu Asn Tyr Asn Gln Thr Ser Thr Asp Phe Ile Leu Leu Gly Phe
 1               5                  10                  15

Phe Pro Pro Ser Arg Ile Gly Leu Phe Leu Phe Ile Leu Ile Val Phe
                20                  25                  30
```

```
Ile Phe Leu Met Ala Leu Ile Gly Asn Leu Ser Met Ile Leu Leu Ile
         35                  40                  45

Phe Leu Asp Thr His Leu His Thr Pro Met Tyr Phe Leu Leu Ser Gln
 50                  55                  60

Leu Ser Leu Ile Asp Leu Asn Tyr Ile Ser Thr Ile Val Pro Lys Met
 65                  70                  75                  80

Ala Ser Asp Phe Leu Ser Gly Asn Lys Ser Ile Ser Phe Thr Gly Cys
                 85                  90                  95

Gly Ile Gln Ser Phe Phe Phe Ser Ala Leu Gly Gly Ala Glu Ala Leu
                100                 105                 110

Leu Leu Ala Ser Met Ala Tyr Asp Arg Tyr Ile Ala Ile Cys Phe Pro
            115                 120                 125

Leu His Tyr Pro Ile Arg Met Ser Lys Arg Met Cys Val Leu Met Ile
        130                 135                 140

Thr Gly Ser Trp Ile Ile Gly Ser Ile Asn Ala Cys Ala His Thr Val
145                 150                 155                 160

Tyr Val Leu His Ile Pro Tyr Cys Gln Ser Arg Ala Ile Asn His Phe
                165                 170                 175

Phe Cys Asp Val Pro Ala Met Val Thr Leu Ala Cys Met Asp Thr Trp
                180                 185                 190

Val Tyr Glu Gly Thr Val Phe Leu Ser Thr Thr Ile Phe Leu Val Phe
            195                 200                 205

Pro Phe Ile Ala Ile Ser Cys Ser Tyr Gly Arg Val Leu Leu Ala Val
        210                 215                 220

Tyr His Met Lys Ser Ala Glu Gly Arg Lys Lys Ala Tyr Leu Thr Cys
225                 230                 235                 240

Ser Thr His Leu Thr Val Val Thr Phe Tyr Tyr Ala Pro Phe Val Tyr
                245                 250                 255

Thr Tyr Leu Arg Pro Arg Ser Leu Arg Ser Pro Thr Glu Asp Lys Val
                260                 265                 270

Leu Ala Val Phe Tyr Thr Thr Leu Thr Pro Met Leu Asn Pro Ile Ile
            275                 280                 285

Tyr Ser Leu Arg Asn Lys Glu Val Met Gly Ala Leu Thr Arg Val Ser
        290                 295                 300

Gln Arg Ile Cys Ser Gly Lys Met
305                 310

<210> SEQ ID NO 3
<211> LENGTH: 2445
<212> TYPE: DNA
<213> ORGANISM: Bos taurus
<220> FEATURE:
<221> NAME/KEY: CDS
<222> LOCATION: (1)..(1047)

<400> SEQUENCE: 3 atg aac ggg acc gag ggc cca aac ttc tac gtg cct ttc tcc aac aag      48
Met Asn Gly Thr Glu Gly Pro Asn Phe Tyr Val Pro Phe Ser Asn Lys
 1               5                  10                  15 acg ggc gtg gtg cgc agc ccc ttc gag gcc ccg cag tac tac ctg gcg      96
Thr Gly Val Val Arg Ser Pro Phe Glu Ala Pro Gln Tyr Tyr Leu Ala
             20                  25                  30 gag cca tgg cag ttc tcc atg ctg gcc gcc tac atg ttc ctg ctg atc     144
Glu Pro Trp Gln Phe Ser Met Leu Ala Ala Tyr Met Phe Leu Leu Ile
         35                  40                  45 atg ctt ggc ttc ccc atc aac ttc ctc acg ctg tac gtc aca gtc cag     192
```

```
Met Leu Gly Phe Pro Ile Asn Phe Leu Thr Leu Tyr Val Thr Val Gln
    50                  55                  60 cac aag aag ctg cgc aca ccc ctc aac tac atc ctg ctc aac ctg gcc         240
His Lys Lys Leu Arg Thr Pro Leu Asn Tyr Ile Leu Leu Asn Leu Ala
65                  70                  75                  80 gtg gcc gac ctc ttc atg gtc ttc ggg ggc ttc acc acc acc ctc tac         288
Val Ala Asp Leu Phe Met Val Phe Gly Gly Phe Thr Thr Thr Leu Tyr
                        85                  90                  95 acc tct ctg cac gga tac ttc gtc ttt ggg ccc acg ggc tgc aac ctg         336
Thr Ser Leu His Gly Tyr Phe Val Phe Gly Pro Thr Gly Cys Asn Leu
                100                 105                 110 gag ggc ttc ttt gcc acc ctg ggc ggt gaa att gca ctg tgg tcc ttg         384
Glu Gly Phe Phe Ala Thr Leu Gly Gly Glu Ile Ala Leu Trp Ser Leu
            115                 120                 125 gtg gtc ctg gcc atc gag cgg tac gtg gtg gtg tgc aag ccc atg agc         432
Val Val Leu Ala Ile Glu Arg Tyr Val Val Val Cys Lys Pro Met Ser
        130                 135                 140 aac ttc cgc ttc ggg gag aac cac gcc atc atg ggc gtc gcc ttc acc         480
Asn Phe Arg Phe Gly Glu Asn His Ala Ile Met Gly Val Ala Phe Thr
145                 150                 155                 160 tgg gtc atg gct ctg gcc tgt gcc gcg ccc ccc ctc gtc ggc tgg tcc         528
Trp Val Met Ala Leu Ala Cys Ala Ala Pro Pro Leu Val Gly Trp Ser
                165                 170                 175 agg tac atc ccg gag ggc atg cag tgc tcg tgc ggg att gac tac tac         576
Arg Tyr Ile Pro Glu Gly Met Gln Cys Ser Cys Gly Ile Asp Tyr Tyr
                180                 185                 190 acg ccc cac gag gag acc aac aat gag tcg ttc gtc atc tac atg ttc         624
Thr Pro His Glu Glu Thr Asn Asn Glu Ser Phe Val Ile Tyr Met Phe
            195                 200                 205 gtg gtc cac ttc atc atc ccc ctg att gtc ata ttc ttc tgc tac ggg         672
Val Val His Phe Ile Ile Pro Leu Ile Val Ile Phe Phe Cys Tyr Gly
        210                 215                 220 cag ctg gtg ttc acc gtc aag gag gcg gct gcc cag cag cag gag tcg         720
Gln Leu Val Phe Thr Val Lys Glu Ala Ala Ala Gln Gln Gln Glu Ser
225                 230                 235                 240 gcc acc act cag aag gcc gag aag gag gtc acc cgc atg gtg atc atc         768
Ala Thr Thr Gln Lys Ala Glu Lys Glu Val Thr Arg Met Val Ile Ile
                245                 250                 255 atg gtc atc gct ttc cta atc tgc tgg ctg ccc tac gct ggg gtg gcg         816
Met Val Ile Ala Phe Leu Ile Cys Trp Leu Pro Tyr Ala Gly Val Ala
                260                 265                 270 ttc tac atc ttc acc cat cag ggc tct gac ttt ggc ccc atc ttc atg         864
Phe Tyr Ile Phe Thr His Gln Gly Ser Asp Phe Gly Pro Ile Phe Met
            275                 280                 285 acc atc ccg gct ttc ttt gcc aag act tct gcc gtc tac aac ccc gtc         912
Thr Ile Pro Ala Phe Phe Ala Lys Thr Ser Ala Val Tyr Asn Pro Val
        290                 295                 300 atc tac atc atg atg aac aag cag ttc cgg aac tgc atg gtc acc act         960
Ile Tyr Ile Met Met Asn Lys Gln Phe Arg Asn Cys Met Val Thr Thr
305                 310                 315                 320 ctc tgc tgt ggc aag aac ccg ctg ggt gac gac gag gcc tcc acc acc        1008
Leu Cys Cys Gly Lys Asn Pro Leu Gly Asp Asp Glu Ala Ser Thr Thr
                325                 330                 335 gtc tcc aag aca gag acc agc cag gtg gcg cct gcc taa gcccctccag        1057
Val Ser Lys Thr Glu Thr Ser Gln Val Ala Pro Ala
                340                 345 ggactccgtg gccagctgca ggagtccctc agccccacc ccaccccagc ctcagcagct        1117
ccatcaggag ccgcgcctgt cggaaccagc tctcacaggc tccctgagtg taaacacaaa      1177
```

```
gaccaaccaa ccaaatgcaa aagaatcaac gagagaaaca ggaggcgcct cacgtggcag    1237
gggcggcccg atctggagtc ctgatttccc gggggcccgc tgtagatcca ctcccccag    1297 ctcatctctc agctacacaa gagctcttgc tctggaaaag tgtcccagct tagggataag    1357
tgagtagcac atgacggggc atgccgtagg tgcttattaa taaatgctag gtggaggaaa    1417
gaaggaatga atggagagat gaacgggtcg ggagggcata ggcatcctct tacaacatgt    1477
tagcagcagc agcagcagct cgccttggc tcatgacctt gagcagctgt tttgtccttg     1537
ggcctcactt tcttccccca tacaatggga attccaaatc tctcctcaca cgggctgctg    1597
ggaagatcaa atgagattgt gtgtgtgtgc gtgcgtgcgt gctcgcttgt gtgagctctt    1657
tgtaaatagt aaggagctgg acagactgta gttaacatta tgaataatat caagtaatat    1717
aagtaattca tctcctatga tcatctcctc ttgatagcga ccactttgag actgggcaag    1777
gctctaagca tccagcctcg tcaggcttat aaacattaga cagatggcaa ggtcagacca    1837
gcgccgggtg gtgggccaca gggaaggacg gtcaaggaaa tgcagagtgc aggcatcagg    1897
cctgagaaga aaacaaaaac caaaaaaaca acatcagagg accagagtct ggggccagtg    1957
cagagccccc atgacgcggg ccactccctc ccagtgcaac ccccagagag acaggtcttg    2017
ctctcggcat ctgaaaaacc actagctctc ctgcccagca cccaggctgc agtatctctg    2077
ggcccgtatg gagcttctag aagttatgtt tacctgccca catttaacga gagctgggt    2137 ccccaacatc acctttgtct caaaaagagc ttaaaaaaca aaagcgtggg aaatccggct    2197
ggacccacct tcccctggg aagttcacag atcacagatt ttagctccct tgctgggcaa    2257
gccttcagcg gctccagtcc attctccact ccggagagtc cttgctgctg agaggctggc    2317
tgggactcta ggacatcaga atcgagccgc ctcataactg ccctcctcc actacataac    2377 caaagcggga agctctacct ctccccagct ctgcctggag acgaaggcaa attggggtat    2437
taaaagct                                                             2445
```

<210> SEQ ID NO 4
<211> LENGTH: 348
<212> TYPE: PRT
<213> ORGANISM: Bos taurus

<400> SEQUENCE: 4

```
Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
            20                  25                  30

Glu Pro Trp Gln Phe Ser Met Leu Ala Ala Tyr Met Phe Leu Leu Ile
        35                  40                  45

Met Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Phe Gly Gly Phe Thr Thr Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
    130                 135                 140
```

-continued

```
Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Val Gly Trp Ser
            165                 170                 175

Arg Tyr Ile Pro Glu Gly Met Gln Cys Ser Cys Gly Ile Asp Tyr Tyr
            180                 185                 190

Thr Pro His Glu Glu Thr Asn Asn Glu Ser Phe Val Ile Tyr Met Phe
        195                 200                 205

Val Val His Phe Ile Ile Pro Leu Ile Val Ile Phe Phe Cys Tyr Gly
        210                 215                 220

Gln Leu Val Phe Thr Val Lys Glu Ala Ala Gln Gln Gln Glu Ser
225                 230                 235                 240

Ala Thr Thr Gln Lys Ala Glu Lys Glu Val Thr Arg Met Val Ile Ile
            245                 250                 255

Met Val Ile Ala Phe Leu Ile Cys Trp Leu Pro Tyr Ala Gly Val Ala
            260                 265                 270

Phe Tyr Ile Phe Thr His Gln Gly Ser Asp Phe Gly Pro Ile Phe Met
            275                 280                 285

Thr Ile Pro Ala Phe Phe Ala Lys Thr Ser Ala Val Tyr Asn Pro Val
            290                 295                 300

Ile Tyr Ile Met Met Asn Lys Gln Phe Arg Asn Cys Met Val Thr Thr
305                 310                 315                 320

Leu Cys Cys Gly Lys Asn Pro Leu Gly Asp Asp Glu Ala Ser Thr Thr
            325                 330                 335

Val Ser Lys Thr Glu Thr Ser Gln Val Ala Pro Ala
            340                 345
```

METHOD FOR SCREENING OF UNPLEASANT ODOR MASKING AGENTS

CROSS-REFERENCE TO RELATED APPLICATIONS

This application claims priority to JP 2020-127591, filed Jul. 28, 2020 and JP 2020-174788, filed Oct. 16, 2020.

The instant application contains a Sequence Listing which has been submitted in ASCII format via EFS-WEB and is hereby incorporated by reference in its entirety. Said ASCII copy, created on Jul. 27, 2021, is named sequence.txt and is 17,814 bytes.

TECHNICAL FIELD

The present invention relates to a method for screening an unpleasant odor masking agent.

BACKGROUND ART

Recently, the population of persons sensitive to bad smells and unpleasant odors around them is growing depending on diversification of consumer preferences and living environments. The range thereof is wide, from odors in living spaces to slight off-flavors contained in foods, and a technique for reducing/masking an unpleasant odor more effectively is desired for the improvement of the quality of life.

Typical examples of substances that cause unpleasant odors in living spaces include skatole and indole which are contained in body odor, fecal odor, rotten odor, etc. (Patent Literature 1).

These unpleasant odor substances are tryptophan metabolites derived from animal protein and generated by in vivo metabolism and microbial metabolism. For this reason, the unpleasant odor substances are contained not only in human body odor and excrement, but also in animal-derived foods such as dairy products, and are one of causes for reducing preference of foods as off-flavors (Non-Patent Literature 1).

Many components are known as substances that cause off-flavors in foods, and examples thereof include α-terpineol, 4-terpineol and p-methylacetophenone, which are deterioration odors derived from citrus or the like (Non-Patent Literature 2).

Conventional methods for searching a substance for reducing/deodorizing an unpleasant odor have a problem of low through-put performance because in such methods, experts of odor evaluation confirm a huge number of candidate substances one by one by sensory evaluation. Meanwhile, according to molecular biological techniques established recently, by searching an olfactory receptor that responds to an unpleasant odor-causing substance and using the olfactory receptor, a candidate substance for an unpleasant odor masking agent can be rapidly screened.

There are about 400 types of human olfactory receptors and one odorous substance responds to many olfactory receptors, while a part of receptors that respond are called broadly tuned olfactory receptors and recognize a wide range of odorous substances without distinction. For this reason, it is important to know which of several receptors to which an unpleasant odor-causing substance responds is highly associated with unpleasantness. For example, Non-Patent Literature 3 reports that an olfactory receptor OR7D4 is a truly important receptor associated with unpleasantness of androstenone odor. Non-Patent Literature 4 describes many broadly tuned olfactory receptors that widely respond regardless of the type of scent such as OR2W1.

Patent Literature 2 discloses OR2W1, OR5P3, OR5K1 and OR8H1 as olfactory receptors that respond to skatole or indole that is an unpleasant odor-causing substance, and describes that skatole odor or indole odor can be suppressed by suppressing responses of these olfactory receptors. Further, Patent Literature 3 discloses that o-isopropylphenol that is an accumulated unpleasant odorous substance generated in transport equipment such as vehicles responds to an olfactory receptor OR2L3.

CITATION LIST

Patent Literatures

Patent Literature 1: Japanese Laid-Open Patent Publication No. 2008-036434
Patent Literature 2: Japanese Laid-Open Patent Publication No. 2012-250958
Patent Literature 3: Japanese Laid-Open Patent Publication No. 2017-176134
Patent Literature 4: Japanese Laid-Open Patent Publication No. 2008-136841

Non-Patent Literatures

Non-Patent Literature 1: J. Agric. Food Chem. 2001, 49, 10, 4825-4832
Non-Patent Literature 2: Nippon Nogeikagaku Kaishi Vol. 55, No. 1, pp. 23-30, 1981
Non-Patent Literature 3: Nature. 2007 Sep. 27; 449 (7161): 468-72
Non-Patent Literature 4: Flavour Fragr. J. 2015, 30, 342-361
Non-Patent Literature 5: Nature Communications 10:209 (2019)

SUMMARY OF INVENTION

Technical Problem

Many of olfactory receptors whose responses to skatole and indole are disclosed are broadly tuned olfactory receptors, and it has been unclear and unknown which of olfactory receptors characterizes the recognition of unpleasant odor. Further, olfactory receptors which clearly respond to α-terpineol, 4-terpineol and p-methylacetophenone have been unknown. Under such circumstances, it is desired to provide: a method for efficiently screening a candidate substance for an unpleasant odor masking agent by searching an olfactory receptor which responds to an unpleasant odor-causing substance typified by skatole, indole, α-terpineol, 4-terpineol and p-methylacetophenone; and an unpleasant odor masking composition for reducing unpleasantness of the unpleasant odor.

Solution to Problem

The present inventor diligently made researches in order to solve the above-described problems and newly found that a certain type of unpleasant odor-causing substance typified by skatole, indole, α-terpineol, 4-terpineol, p-methylacetophenone, etc. characteristically responds to an olfactory receptor OR2L3. When summarizing results of the response of OR2L3 to several hundred types of odorous substances, a new finding that substances responsive to OR2L3 include a certain number of unpleasant odor substances was obtained. Based on this, OR2L3 was specified as an olfactory receptor important for recognizing unpleasant odors. The present inventor further made researches and found that the evaluation and selection of an unpleasant odor masking agent utilizing the masking effect of an olfactory receptor antagonist can be carried out by using OR2L3.

Specifically, the present invention provides a method for screening a candidate substance for a masking agent for unpleasant odors responsive to OR2L3 typified by skatole, indole, α-terpineol, 4-terpineol, p-methylacetophenone, etc. described below.

[1] A method for screening an unpleasant odor masking agent, comprising the steps of:
  adding a test substance and an unpleasant odor-causing substance to an olfactory receptor polypeptide selected from the group consisting of OR2L3 and polypeptides which comprise an amino acid sequence having at least 80% identity to an amino acid sequence of OR2L3 and are responsive to the unpleasant odor-causing substance;
  measuring a response of the olfactory receptor polypeptide to the unpleasant odor-causing substance; and
  identifying the test substance that suppresses the response of the olfactory receptor polypeptide based on the measured response, i.e., identifying the test substance that suppresses the response of the olfactory receptor polypeptide as a candidate substance for the unpleasant odor masking agent based on the measured response.

[2] The method according to item [1], wherein the unpleasant odor is skatole odor, indole odor, α-terpineol odor, 4-terpineol odor or p-methylacetophenone odor.

[3] The method according to item [1], wherein the unpleasant odor is fecal odor, breath odor, dairy product-derived deterioration odor or citrus-derived deterioration odor.

[4] The method according to item [1], wherein the unpleasant odor is an odor from a compound, composition or mixture that is unpleasant for humans.

[5] The method according to any one of items [1] to [4], wherein the response of the olfactory receptor polypeptide to the unpleasant odor-causing substance is measured on a cell isolated from a living body in which the olfactory receptor is expressed, or on a cell in which the olfactory receptor is artificially expressed by means of genetic engineering.

[6] The method according to any one of items [1] to [5], wherein the response of the olfactory receptor is measured by means of reporter gene assay or calcium imaging.

Advantageous Effects of Invention

By using the method of the present invention, it is possible to screen a candidate substance for an unpleasant odor masking agent that can inhibit bonding between an unpleasant odor-causing substance and an olfactory receptor OR2L3. Further, even when a target unpleasant odor is a mixture, wherein a causing substance thereof is unspecified, the possibility that a test substance responds to OR2L3 can be easily inferred, and therefore, as long as just the response of OR2L3 is confirmed, the method for screening an unpleasant odor masking agent can also be applied to identify selective masking substances against an unidentified unpleasant odor substance efficiently. It is expected that the similar effects can be obtained when using a polypeptide which comprise an amino acid sequence having at least 80% identity to an amino acid sequence of OR2L3 and is responsive to the unpleasant odor-causing substance as an olfactory receptor.

DESCRIPTION OF EMBODIMENTS

Figure 1:
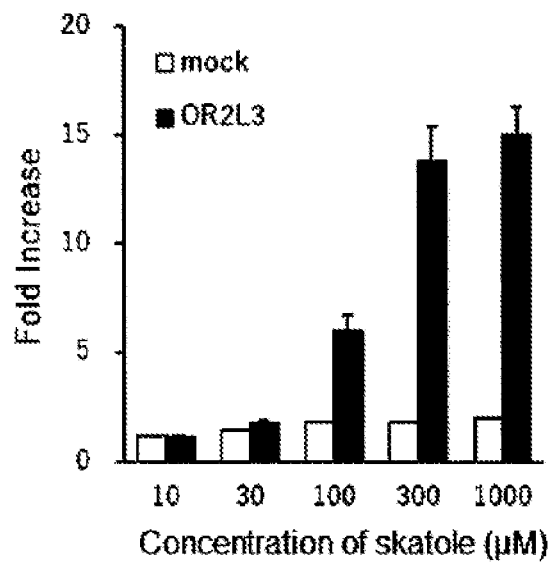
FIG. 1 shows measurement results of the response of the olfactory receptor OR2L3 to skatole.
Figure 2:
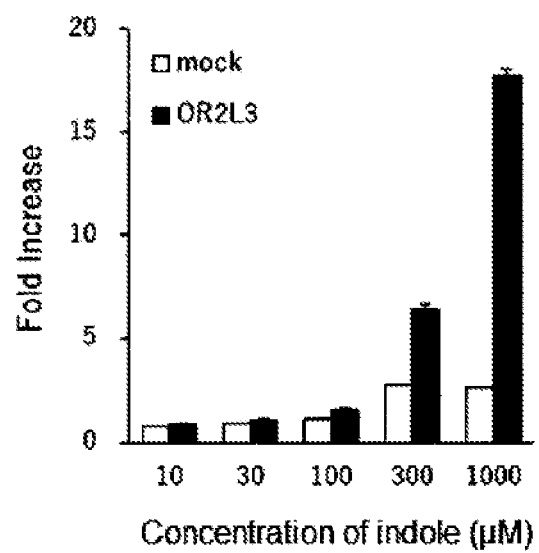
FIG. 2 shows measurement results of the response of the olfactory receptor OR2L3 to indole.
Figure 3:
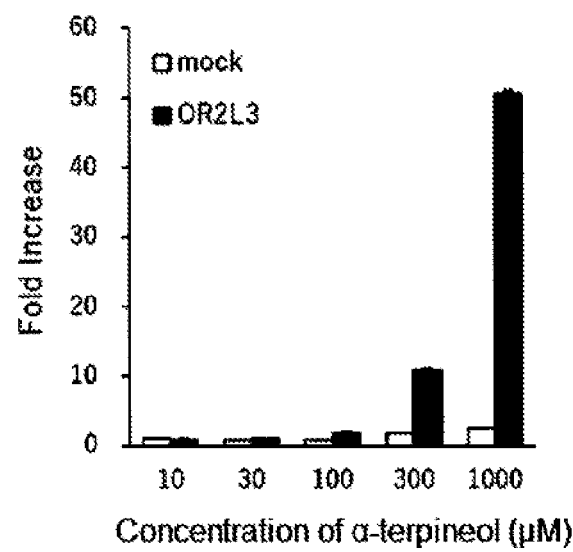
FIG. 3 shows measurement results of the response of the olfactory receptor OR2L3 to α-terpineol.
Figure 4:
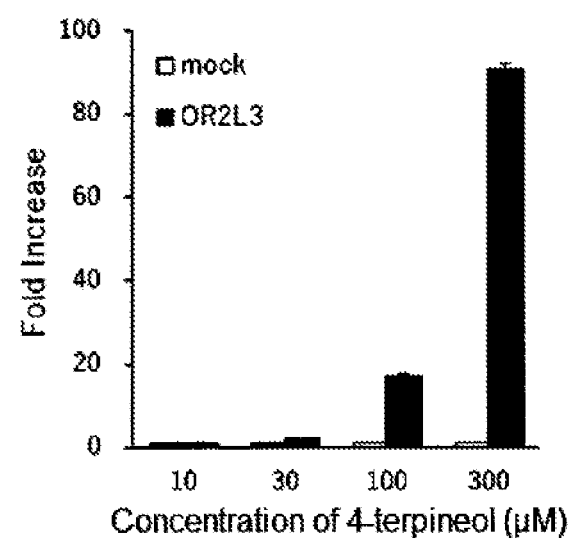
FIG. 4 shows measurement results of the response of the olfactory receptor OR2L3 to 4-terpineol.
Figure 5:
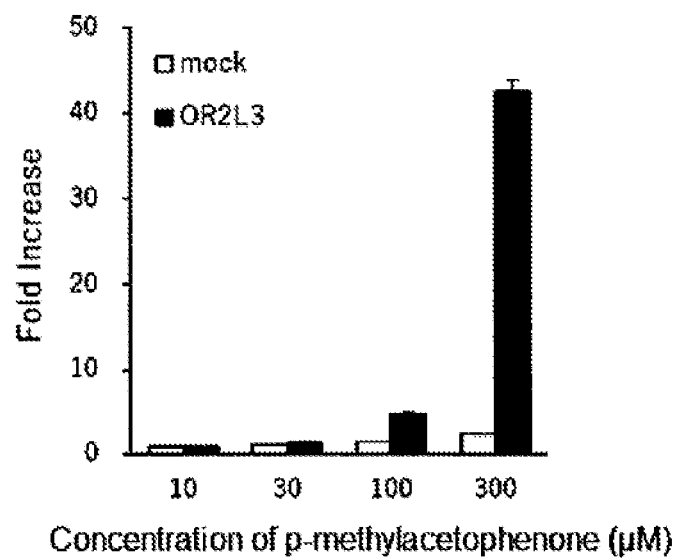
FIG. 5 shows measurement results of the response of the olfactory receptor OR2L3 to p-methylacetophenone.

Hereinafter, the screening method of the present invention will be specifically described.

As described above, the screening method of the present invention includes:
  adding a test substance and an unpleasant odor-causing substance to an olfactory receptor polypeptide selected from the group consisting of OR2L3 and polypeptides which comprise an amino acid sequence having at least 80% identity to an amino acid sequence of OR2L3 and are responsive to the unpleasant odor-causing substance;
  measuring a response of the olfactory receptor polypeptide to the unpleasant odor-causing substance; and
  identifying the test substance that suppresses the response of the olfactory receptor polypeptide as a candidate substance for the unpleasant odor masking agent based on the measured response.

The present invention can be practiced, for example, according to the below-described embodiments.

In one embodiment, the present invention is characterized in that it is a method for screening a candidate substance for an unpleasant odor masking agent from among test substances using an olfactory receptor OR2L3 that is responsive to an unpleasant odor-causing substance, which includes the steps of:

(i) bringing the unpleasant odor-causing substance into contact with the olfactory receptor (olfactory receptor polypeptide) selected from the group consisting of OR2L3 and proteins (polypeptides) which comprise an amino acid sequence having at least 80% identity to an amino acid sequence of OR2L3 and are responsive to the unpleasant odor-causing substance to measure a response of the olfactory receptor to the unpleasant odor-causing substance;

(ii) measuring a response of the olfactory receptor used in the step (i) in the absence of the unpleasant odor-causing substance;

(iii) obtaining a change value of responsiveness by making a calculation based on comparison between measurement results in the steps (i) and (ii);

(iv) mixing each of the test substances separately with the unpleasant odor-causing substance in the step (i) and obtaining a change value of responsiveness by making a calculation in a manner similar to that in the step (iii); and (v) selecting a test substance, regarding which the value of the step (iv) is reduced when compared to the value of the step (iii), as the candidate substance for the unpleasant odor masking agent.

In the screening method of the present invention, a candidate substance for an unpleasant odor masking agent is selected from among test substances, using the responsiveness of the test substances to an olfactory receptor selected from the group consisting of an olfactory receptor OR2L3 and proteins (polypeptides) which comprise an amino acid sequence having at least 80% identity to an amino acid sequence of OR2L3 and are responsive to an unpleasant odor-causing substance as an index.

It is known that when one odorous substance activates a plurality of olfactory receptors, emotions and behaviors such as likes or dislikes and attraction or avoidance are generally caused. Non-Patent Literature 5 shows that the "quality" of an odor is defined in each olfactory receptor. When the response of OR2L3 to several hundred types of odorous substances was measured and diligently researched and summarized, since substances responsive to OR2L3 include a certain number of unpleasant odor substances, OR2L3 was associated with recognition of unpleasant odors corresponding to dislikes and avoidance. Accordingly, by evaluating the responsiveness of test substances to the olfactory receptor OR2L3, a candidate substance which can inhibit bonding between an unpleasant odor-causing substance and the olfactory receptor can be selected from among the test substances.

Note that in this specification, the "test substance" is not particularly limited, but means a target to be researched with respect to the unpleasant odor masking effect and means a compound, composition or mixture. Further, in this specification, the "unpleasant odor masking agent" is not particularly limited, but means a compound, composition or mixture capable of masking an unpleasant odor. Hereinafter, each step of the screening method of the present invention will be described.

<Step (i)>

In the step (i), an unpleasant odor-causing substance is brought into contact with an olfactory receptor selected from the group consisting of OR2L3 and proteins (polypeptides) which comprise an amino acid sequence having at least 80% identity to an amino acid sequence of OR2L3 and are responsive to the unpleasant odor-causing substance to measure a response of the olfactory receptor to the unpleasant odor-causing substance.

As the olfactory receptor, one selected from the group consisting of OR2L3 and proteins (polypeptides) which comprise an amino acid sequence having at least 80% identity to an amino acid sequence of OR2L3 and are responsive to the unpleasant odor-causing substance is used.

OR2L3 has been registered in GenBank as NM_001004687 and is a protein (polypeptide) consisting of an amino acid sequence (SEQ ID NO: 2) encoded by DNA of a nucleotide sequence represented by SEQ ID NO: 1.

Since the olfactory receptor OR2L3 selectively responds to a certain type of unpleasant odor substance typified by skatole, it is expected that the screening method using OR2L3 can contribute to the development of unpleasant odor masking agents.

As the olfactory receptor, one selected from the group consisting of proteins (polypeptides) which comprise an amino acid sequence having at least 80%, preferably at least 85%, more preferably at least 90%, even more preferably at least 95%, and particularly preferably at least 98% identity to an amino acid sequence of OR2L3 and are responsive to an unpleasant odor-causing substance may be used. Note that in this specification, the sequence identity of an amino acid sequence is calculated using the BLAST search algorithm (publicly available from NCBI).

As the olfactory receptor, one material may be used solely, or two or more materials may be used in combination.

In the present invention, the unpleasant odor-causing substance is fecal odor, breath odor, dairy product-derived deterioration odor or citrus-derived deterioration odor typified by skatole, indole, α-terpineol, 4-terpineol or p-methylacetophenone, and means an OR2L3-responsive compound, composition or mixture that is unpleasant for humans.

In the present invention, the method of bringing the unpleasant odor-causing substance into contact with the olfactory receptor to measure the response of the olfactory receptor to the unpleasant odor-causing substance is not particularly limited. For example, the response of the olfactory receptor may be measured by carrying out the contact with the unpleasant odor-causing substance on a cell isolated from a living body in which the olfactory receptor is expressed. Alternatively, the response of the olfactory receptor may be measured by carrying out the contact with the unpleasant odor-causing substance on a cell in which the olfactory receptor is artificially expressed by means of genetic engineering. The time for the contact between the olfactory receptor and the unpleasant odor-causing substance cannot be categorically described because it depends on the concentration of the unpleasant odor-causing substance and the measurement method, but the response may be measured immediately after the contact. Generally, in the reporter gene assay method, the time is 0 to 4 hours, and preferably 2 to 4 hours, and in the calcium imaging method, the time is about several seconds to several minutes.

The cell in which the olfactory receptor is artificially expressed by means of genetic engineering can be prepared by transforming a cell with use of a vector in which a gene encoding the olfactory receptor is incorporated.

In a preferred embodiment of the present invention, the N-terminal 20 amino acid residues of bovine rhodopsin may be incorporated together with the olfactory receptor. By incorporation of the N-terminal 20 amino acid residues of bovine rhodopsin, cell membrane expression of the olfactory receptor can be promoted.

Bovine rhodopsin has been registered in GenBank as NM_001014890. Bovine rhodopsin is a protein (polypeptide) consisting of an amino acid sequence (SEQ ID NO: 4)

encoded by DNA of from position 1 to position 1047 of a nucleotide sequence represented by SEQ ID NO: 3.

Further, instead of bovine rhodopsin, a protein (polypeptide) which comprises an amino acid sequence having at least 80%, preferably at least 85%, more preferably at least 90%, even more preferably at least 95%, and particularly preferably at least 98% identity to the amino acid sequence represented by SEQ ID NO: 4 and can promote cell membrane expression of the olfactory receptor may be used.

Note that amino acid residues of a protein (polypeptide) other than bovine rhodopsin may also be used as long as it can promote cell membrane expression of the olfactory receptor.

The method for measuring the response of the olfactory receptor is not particularly limited, and any method used in the art may be used. For example, it is known that when an aroma compound binds to an olfactory receptor, a G-protein in a cell is activated, the G-protein activates adenylate cyclase to convert ATP into cyclic AMP (CAMP), and the amount of CAMP in the cell is increased thereby. Accordingly, by measuring the amount of cAMP, the response of the olfactory receptor can be measured. As the method for measuring the amount of CAMP, an ELISA method, a reporter gene assay method or the like is used. It is particularly preferred that the response of the olfactory receptor is measured by a reporter gene assay method in which a luminescent substance such as luciferase is used.

<Step (ii)>

In the step (ii), the response of the olfactory receptor used in the step (i) is measured in the absence of the unpleasant odor-causing substance.

As the method for measuring the response of the olfactory receptor, the same method as that in the step (i) can be used, except that the unpleasant odor-causing substance is not brought into contact with the olfactory receptor. For example, the response of the olfactory receptor may be measured on a cell isolated from a living body in which the olfactory receptor is expressed. Alternatively, the response of the olfactory receptor may be measured on a cell in which the olfactory receptor is artificially expressed by means of genetic engineering. For appropriate comparison between measurement results in the steps (i) and (ii), measurement conditions in the steps (i) and (ii) are preferably the same except for the presence or absence of contact with the unpleasant odor-causing substance.

<Step (iii)>

In the step (iii), a change value of responsiveness is obtained by making a calculation based on comparison between measurement results in the steps (i) and (ii).

According to one embodiment of the present invention, the change of responsiveness may be evaluated based on a Fold Increase value, which is obtained by dividing the measurement result in the step (i) by the measurement result in the step (ii), as an index. For example, when the response of the olfactory receptor is measured by a reporter gene assay method in which a luminescent substance such as luciferase is used, the evaluation can be made using an unpleasant odor-causing substance having a concentration with which the Fold Increase value becomes preferably at least 2, more preferably at least 4, and even more preferably at least 10.

<Step (iv)>

In the step (iv), test substances are mixed with the unpleasant odor-causing substance in the step (i) and a change value of responsiveness is obtained by making a calculation in a manner similar to that in the step (iii).

<Step (v)>

In the step (v), a test substance, regarding which the value of the step (iv) is reduced when compared to the value of the step (iii), is selected as a candidate substance for the unpleasant odor masking agent.

In the present invention, when the measurement results in the steps (iii) and (iv) are compared to each other and reduction in the change value of responsiveness is shown, the test substance used in the step (iv) can be evaluated as a candidate substance for the unpleasant odor masking agent.

In the above-described manner, a candidate substance for the unpleasant odor masking agent can be screened from test substances. According to the present invention, a candidate substance for the unpleasant odor masking agent can be selected from many test substances without problems caused by organoleptic evaluation, such as olfactory fatigue and individual difference.

The selected substance can be used as the candidate substance for the unpleasant odor masking agent. Based on the selected substance, modification or the like can be carried out according to need to develop a novel compound having an optimum odor. Moreover, by blending the selected substance with another fragrance material, an unpleasant odor can be suppressed and a fragrance material having an optimum odor can be developed. Use of the screening method of the present invention can contribute to the development of a novel fragrance material for the unpleasant odor masking agent.

EXAMPLES

Hereinafter, the present invention will be described in more detail by way of examples. However, the present invention is not limited to the examples.

Example 1

Confirmation of Response of Olfactory Receptor OR2L3 to Unpleasant Odor-Causing Substance (1) Cloning of Olfactory Receptor Gene A human olfactory receptor gene was obtained by cloning according to the PCR method using Human Genomic DNA: Female (Promega) based on the sequence information registered in GenBank. The N-terminal 20 amino acid residues of bovine rhodopsin were incorporated into a pME18S vector, and the obtained human olfactory receptor gene was further incorporated downstream thereof, thereby obtaining a human olfactory receptor gene expression vector.

(2) Expression of Olfactory Receptor Gene in HEK293T Cells 0.05 µg of the human olfactory receptor gene expression vector, 0.01 µg of an RTP1S vector, 0.01 µg of a firefly luciferase vector pGL4.29 containing a cAMP-responsive sequence promoter (Promega), and 0.005 µg of a *Renilla* luciferase vector pGL4.74 containing a thymidine kinase promoter (Promega) were dissolved in 10 µL of Opti-MEM I (gibco) to obtain a gene solution (for one well). 100 µL of HEK293T cells were seeded in each well of a 96-well plate (Biocoat manufactured by Corning) so as to reach confluency after 24 hours. According to the directions for use of Lipofectamine 3000, by the lipofection method, the gene solution was added to each well to perform gene transfer to cells, and culturing was performed under 5% carbon dioxide atmosphere at 37° C. for 24 hours.

(3) Luciferase Reporter Gene Assay

After removing the culture medium, 50 μL of CD293 medium (gibco) (20 μM L-glutamine added) including measured concentration of an aroma compound as a sample was added to each well, and stimulation was performed for 3 hours. After that, the luciferase activity was measured according to the directions for use of Dual-Luciferase Reporter Assay System (Promega). The response strength of the olfactory receptor was expressed by the Fold Increase value, which is obtained by dividing the luciferase activity generated by stimulation of the aroma compound by the luciferase activity generated in the test system not including the aroma compound.

(4) Identification of Olfactory Receptor Responsive to Unpleasant Odor Substance Responses of the olfactory receptor OR2L3 to skatole, indole, α-terpineol, 4-terpineol or p-methylacetophenone as a typical example of the unpleasant odor-causing substance were measured with various concentrations by means of luciferase reporter gene assay. The results are shown in FIGS. 1 to 5. OR2L3 showed concentration-dependent responses to the respective unpleasant odor-causing substances. Meanwhile, in the Mock test (using cells in which OR2L3 was not expressed), no response was shown. That is, it was shown that OR2L3 specifically responds to the respective unpleasant odor-causing substances.

Example 2

Figure 6:
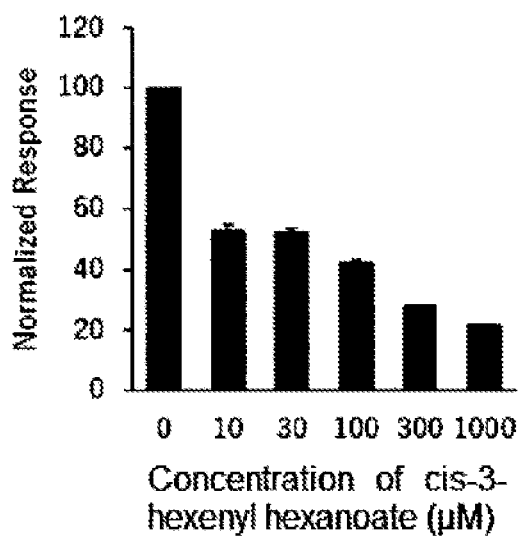
FIG. 6 shows the effect of suppressing the response of the olfactory receptor OR2L3 to skatole obtained by the addition of cis-3-hexenyl hexanoate.

Evaluation of Effect of Suppressing Response of OR2L3 with Respect to Unpleasant Odor Masking Agent With respect to cis-3-hexenyl hexanoate, which is known as a skatole odor masking agent that masks skatole odor in Patent Literature 4, the effect of suppressing the response of OR2L3 that strongly responded to skatole was measured by means of luciferase reporter gene assay. In luciferase reporter gene assay, skatole and cis-3-hexenyl hexanoate were used by being mixed with a sample. The Fold Increase value in the test in which cis-3-hexenyl hexanoate was not mixed was regarded as 100, and the ratio of the Fold Increase value in the test in which cis-3-hexenyl hexanoate was mixed was obtained. The results are shown in FIG. 6. The effect of concentration-dependently reducing the response of OR2L3 to skatole exerted by cis-3-hexenyl hexanoate was shown.

Example 3

Evaluation of Effect of Suppressing Response of OR2L3 with Respect to Unpleasant Odor Masking Agents (Group of Candidate Substances)

With respect to unpleasant odor masking agents (group of candidate substances) including Group A shown in Table 1, the effects of suppressing the response of OR2L3 that strongly responded to unpleasant odors were measured by means of luciferase reporter gene assay.

Figure 7:
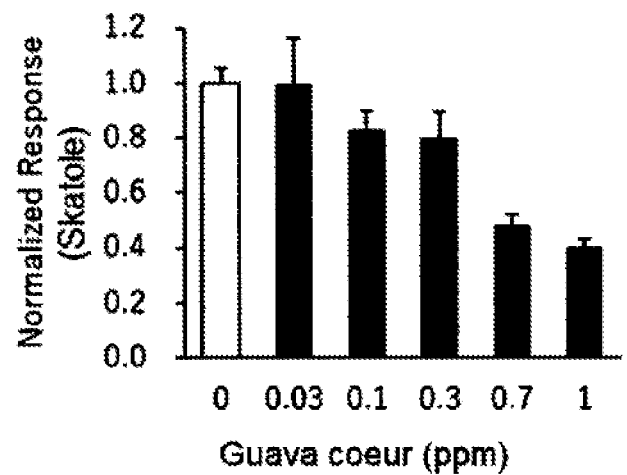
FIG. 7 shows the effect of suppressing the response of the olfactory receptor OR2L3 to skatole obtained by the addition of Guava coeur (Ethyl 3-mercapto-2-methylbutyrate).

In luciferase reporter gene assay, skatole and Guava coeur (Ethyl 3-mercapto-2-methylbutyrate) were used by being mixed with a sample. The Fold Increase value in the test in which Guava coeur was not mixed was regarded as 1, and the ratio of the Fold Increase value in the test in which Guava coeur was mixed was obtained. The results are shown in FIG. 7. The effect of concentration-dependently reducing the response of OR2L3 to skatole exerted by Guava coeur was shown.

Figure 8:
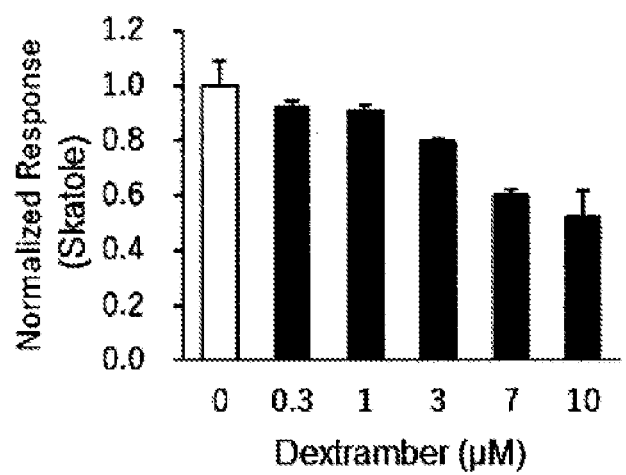
FIG. 8 shows the effect of suppressing the response of the olfactory receptor OR2L3 to skatole obtained by the addition of Dextramber® (1-(2,2,6-trimethylcyclohexyl) hexan-3-ol, registered trademark).
Figure 9:
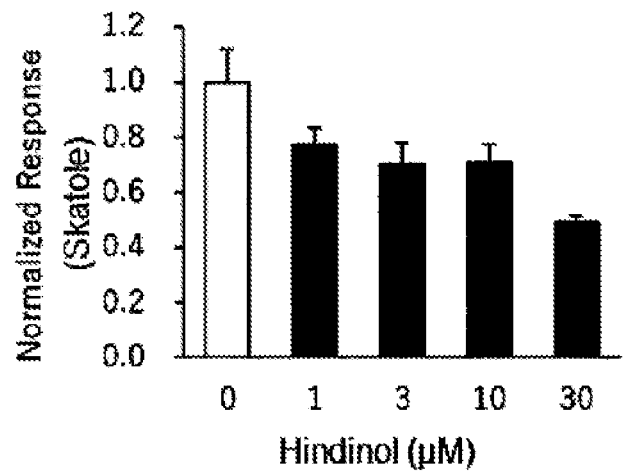
FIG. 9 shows the effect of suppressing the response of the olfactory receptor OR2L3 to skatole obtained by the addition of Hindinol® (2-methyl-4-(2,2,3-trimethyl-3-cyclopentenyl)-2-buten-1-ol, registered trademark).

Guava coeur in the evaluation of the effect of suppressing the response of OR2L3 was replaced by Dextramber® (1-(2,2,6-trimethylcyclohexyl) hexan-3-ol, registered trademark), and the test was conducted in the same manner. The results are shown in FIG. 8. The effect of concentration-dependently reducing the response of OR2L3 to skatole exerted by Dextramber® was shown. Similarly, Guava coeur was replaced by Hindinol® (2-methyl-4-(2,2,3-trimethyl-3-cyclopentenyl)-2-buten-1-ol, registered trademark) and the test was conducted. The results are shown in FIG. 9. The effect of concentration-dependently reducing the response of OR2L3 to skatole exerted by Hindinol® was shown.

Figure 10:
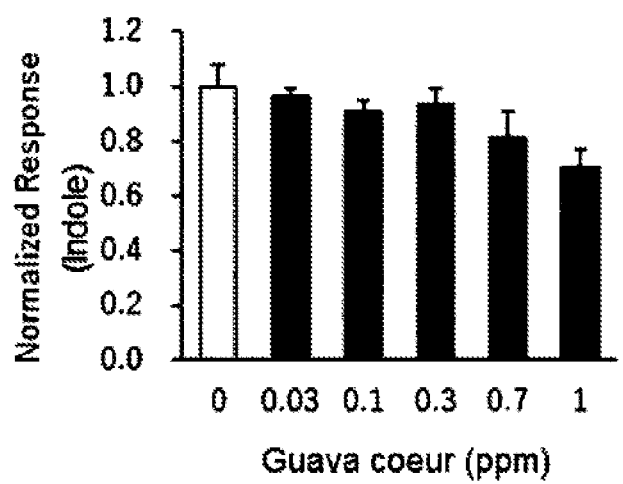
FIG. 10 shows the effect of suppressing the response of the olfactory receptor OR2L3 to indole obtained by the addition of Guava coeur (Ethyl 3-mercapto-2-methylbutyrate).
Figure 11:
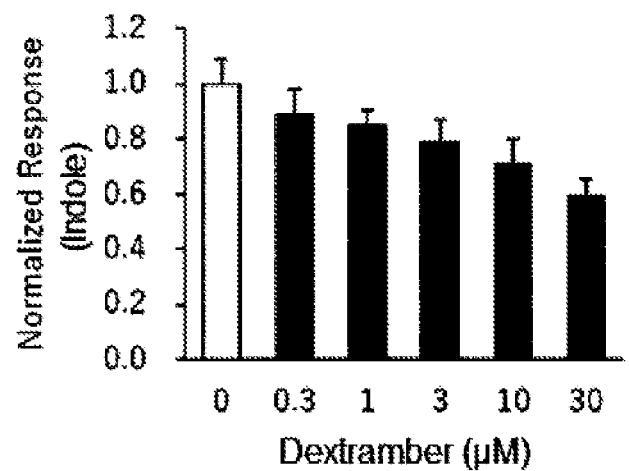
FIG. 11 shows the effect of suppressing the response of the olfactory receptor OR2L3 to indole obtained by the addition of Dextramber® (1-(2,2,6-trimethylcyclohexyl) hexan-3-ol, registered trademark).
Figure 12:
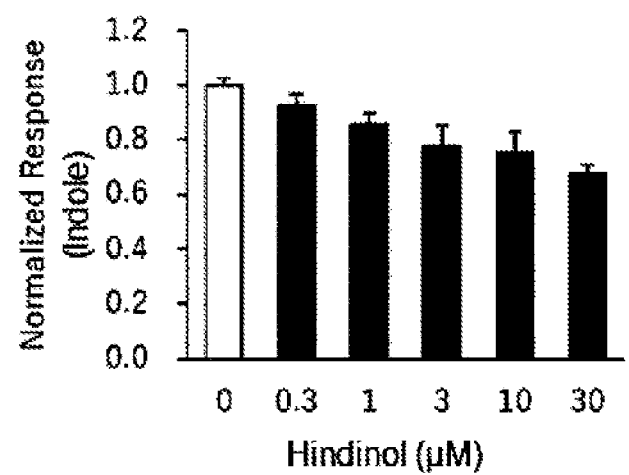
FIG. 12 shows the effect of suppressing the response of the olfactory receptor OR2L3 to indole obtained by the addition of Hindinol® (2-methyl-4-(2,2,3-trimethyl-3-cyclopentenyl)-2-buten-1-ol, registered trademark).

Regarding the unpleasant odor in the evaluation of the effect of suppressing the response of OR2L3, skatole was replaced by indole, and the test was conducted in the same manner. The results obtained by using Guava coeur, Dextramber® and Hindinol®, respectively, as Group A are shown in FIGS. 10 to 12. The effects of concentration-dependently reducing the response of OR2L3 to indole exerted by Guava coeur, Dextramber® and Hindinol® were shown.

In the evaluation of the effect of suppressing the response of OR2L3, the test was further conducted using combinations in which Guava coeur was replaced by another material of Group A and the skatole as the unpleasant odor was replaced by α-terpineol, 4-terpineol or p-methylacetophenone. The effects of concentration-dependently reducing the response of OR2L3 to the respective unpleasant odors exerted by all the materials of Group A were shown.

TABLE 1

| Group A Compound name |
| --- |
| Methyl fenchol (Humus Ether ® (registered trademark)) |
| Ethyl 3-mercapto-2-methylbutyrate (Guava coeur) |
| Dimethyl-2-(1-phenylethyl)cyclopropylmethanol (Pamplefix) |
| 5-cyclohexadecenone (Ambretone ® (registered trademark)) |
| 1-(2,2,6-trimethylcyclohexyl)hexan-3-ol (Dextramber ® (registered trademark)) |
| 2-methyl-4-(2,2,3-trimethyl-3-cyclopentenyl)-2-buten-1-ol (Hindinol ® (registered trademark)) |
| p-mentha-8-thiol-3-one (Ringonol ® (registered trademark)) |
| Cardamom oil |
| Clary sage oil |
| Mandarin oil |
| Spearmint oil |

Example 4

Evaluation of Unpleasant Odor Suppression Ability of Group A

The unpleasant odor suppression ability of test substances having activity to inhibit receptor action was confirmed by sensory evaluation. A cotton ball on which 10 μL of skatole or indole diluted 100-fold with triethyl citrate as an unpleasant odor and 1 μL of a test substance were dropped was put into a plastic bottle (OZO-40 manufactured by Takemoto Yohki Co., Ltd.). The bottle was allowed to stand at room temperature for 1 hour to sufficiently volatilize odor molecules therein. The sensory evaluation test was conducted by a panel consisting of 20 persons, who made evaluation as follows: the odor strength in the case where the unpleasant odor was dropped solely was rated as 8, and the unpleasant odor strength in the case where the test substance was mixed was rated as from 0 (the unpleasant odor is not smelled) to 10 (the unpleasant odor is smelled very strongly). The average value was calculated from obtained numerical values. The results are shown in Table 2.

Humus Ether® (methyl fenchol, registered trademark), which suppresses the response of OR2L3 to skatole, significantly suppressed the strength of skatole odor. This suppression of skatole was remarkable when compared to the cases of using a control substance (4-t-butylcyclohexanol, hexyl salicylate) which did not suppress the response of OR2L3 to skatole. Further, the case of indole was examined, and Humus Ether® also suppressed the strength of indole odor. Note that when the effect of suppressing the unpleasant odors was tested also with respect to other substances that suppress the response of OR2L3 (Guava coeur (Ethyl 3-mercapto-2-methylbutyrate), Pamplefix (Dimethyl-2-(1-phenylethyl)cyclopropylmethanol), Ambretone® (5-cyclohexadecenone), Dextramber® (1-(2,2,6-trimethylcyclohexyl)hexan-3-ol), Hindinol® (2-methyl-4-(2,2,3-trimethyl-3-cyclopentenyl)-2-buten-1-ol), Ringonol® (p-mentha-8-thiol-3-one), cardamom oil, clary sage oil, mandarin oil and spearmint oil), it became clear that all the substances suppress the unpleasant odors.

TABLE 2

| Fragrance substance | Skatole strength | Indole strength |
|---|---|---|
| Unpleasant odor alone | 8.0 | 8.0 |
| Methyl fenchol (Humus Ether ® (registered trademark)) | 3.3 | 3.1 |
| Ethyl 3-mercapto-2-methylbutyrate (Guava coeur | 3.0 | 3.3 |
| Dimethyl-2-(1-phenylethyl)cyclopropylmethanol (Pamplefix) | 2.5 | 2.4 |
| 5-cyclohexadecenone (Ambretone ® (registered trademark)) | 4.2 | 3.6 |
| 1-(2,2,6-trimethylcyclohexyl)hexan-3-ol (Dextramber ® (registered trademark)) | 4.0 | 3.9 |
| 2-methyl-4-(2,2,3-trimethyl-3-cyclopentenyl)-2-buten-1-ol (Hindinol ® (registered trademark)) | 3.6 | 4.1 |
| p-mentha-8-thio1-3-one (Ringonol ® (registered trademark)) | 3.9 | 3.7 |
| Cardamom oil | 4.5 | 4.0 |
| Clary sage oil | 3.3 | 3.2 |
| Mandarin oil | 3.6 | 4.2 |
| Spearmint oil | 3.2 | 3.0 |
| 4-t-butyleyclohexanol | 6.3 | 6.0 |
| Hexyl salicylate | 6.9 | 6.7 |

As described above, by using the screening method of the present invention, a candidate substance for the unpleasant odor masking agent was successfully selected from many test substances.

INDUSTRIAL APPLICABILITY

By using the screening method of the present invention, a candidate substance for the unpleasant odor masking agent can be selected from many test substances. It is expected that the screening method of the present invention can contribute to the development of unpleasant odor masking agents.

The invention claimed is:

1. A method for screening an unpleasant odor masking agent, comprising the steps of:
adding a test substance and an unpleasant odor-causing substance to olfactory receptor OR2L3 (SEQ ID NO: 2);
measuring a response of OR2L3 to the unpleasant odor-causing substance; and
identifying the test substance that suppresses the response of OR2L3 as a candidate substance for the unpleasant odor masking agent based on the measured response,
wherein the unpleasant odor is fecal odor, breath odor, dairy product-derived deterioration odor or citrus-derived deterioration odor.

2. The method according to claim 1, wherein the unpleasant odor is skatole odor, indole odor, α-terpineol odor, 4-terpineol odor or p-methylacetophenone odor.

3. The method according to claim 1, wherein the response of the olfactory receptor polypeptide to the unpleasant odor-causing substance is measured on a cell isolated from a living body in which the olfactory receptor is expressed, or on a cell in which the olfactory receptor is artificially expressed by means of genetic engineering.

4. The method according to claim 1, wherein the response of the olfactory receptor is measured by means of reporter gene assay or calcium imaging.

* * * * *